(12) United States Patent
Beach et al.

(10) Patent No.: US 6,969,843 B1
(45) Date of Patent: Nov. 29, 2005

(54) LIGHT STANDARD FOR MICROSCOPY

(76) Inventors: James M. Beach, 2714 Tidewater Dr., Slidell, LA (US) 70458; Robert A. Ross, 135 Apple La., Charlottesville, VA (US) 22903; Josef K. Hudson, 146 A Buckingham Cir., Charlottesville, VA (US) 22903

( * ) Notice: Subject to any disclaimer, the term of this patent is extended or adjusted under 35 U.S.C. 154(b) by 303 days.

(21) Appl. No.: 10/273,332

(22) Filed: Oct. 17, 2002

Related U.S. Application Data

(60) Provisional application No. 60/346,804, filed on Oct. 19, 2001.

(51) Int. Cl.[7] .............................................. G01J 1/04
(52) U.S. Cl. ...................... 250/228; 250/205; 356/230; 356/236; 362/276
(58) Field of Search ................................. 250/205, 228, 250/216, 201.3; 315/121, 182, 183; 356/230, 356/236; 362/276, 293

(56) References Cited

U.S. PATENT DOCUMENTS

| | | | |
|---|---|---|---|
| 5,489,771 A | 2/1996 | Beach et al. | |
| 6,222,623 B1 * | 4/2001 | Wetherell | 356/236 |
| 6,608,293 B2 * | 8/2003 | Kuderer | 250/200 |

* cited by examiner

Primary Examiner—Kevin Pyo
(74) Attorney, Agent, or Firm—Jagtiani + Guttag

(57) ABSTRACT

The disclosed light standard system provides flat field illumination through the use of an integrating light chamber which is in communication with a microprocessor. The light chamber has at least one high performance light source, such as LED's, recessed within the walls and positioned to prevent light from directly exiting the chamber. A photosensor monitors multiple parameters within the chamber and interacts with the microprocessor to control intensity, temperature and wavelengths. The lights standard operates in benchmark, ratio light, linearity and transient response modes with all parameters being programmable and storable within said microprocessor.

20 Claims, 9 Drawing Sheets

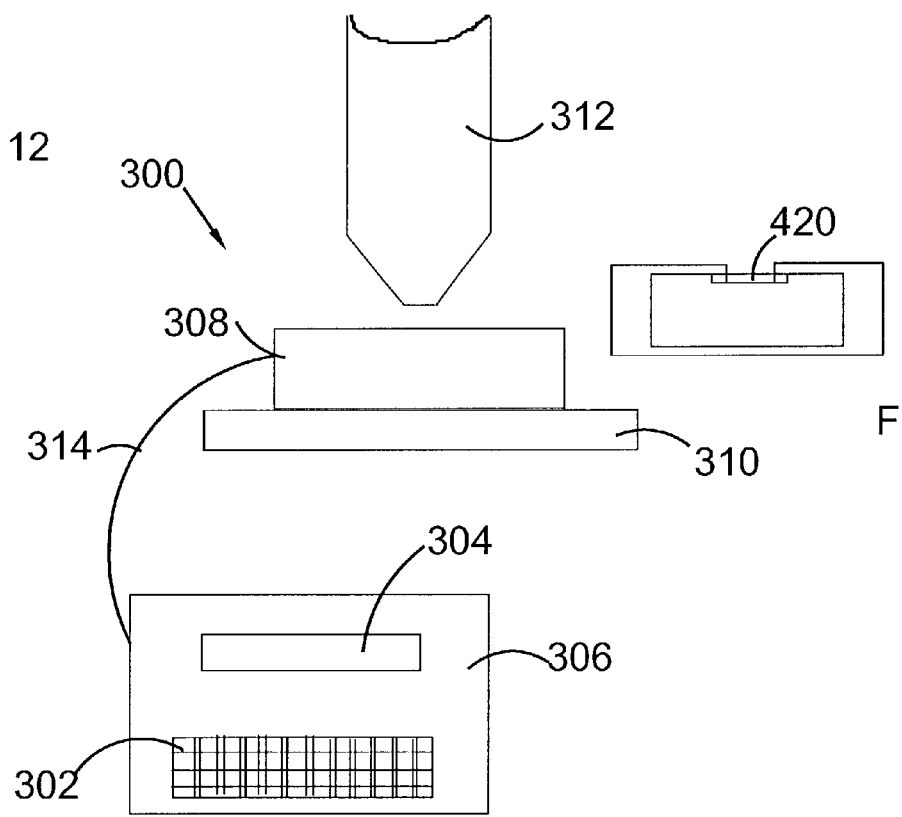

LIGHT STANDARD FOR MICROSCOPY

CROSS-REFERENCE TO RELATED PATENT APPLICATION

The present application claims the benefits under 35 U.S.C. 119(e) of provisional patent application Ser. No. 60/346,804, filed Oct. 19, 2001. This application incorporates by reference, as though recited in full, the disclosure of provisional application 60/346,804, now abandoned.

FIELD OF THE INVENTION

This invention relates to a light standard for a microscope that provides controlled intensity that is traceable to NIST radiometric standards.

BACKGROUND OF THE INVENTION

Limitations of Technology in Quantitative Microscope

Where photo- or video-microscopy are employed as analytical techniques, a light standard providing preset levels of illumination over a homogeneous field covering the viewing area of a microscope is a useful accessory for system validation and testing. Functional studies of cell biology routinely seek information about cellular activity by means of video imaging, using image sequences to monitor correlated cellular actions, such as calcium flux transients in relation to force generation in muscle cells. Quantitative information concerning intracellular ion concentration changes is obtained using ratio imaging techniques, permitting degrees of cellular activity to be compared. The reliability of photomicroscopic assays depends on accurate translation of light intensities, some of which are exceedingly faint, into pixel brightness levels. Unfortunately, video detection systems and accessories employed for low light recording cause distortions of both brightness and geometry in the image. Photoelectron multipliers in SIT and intensified SIT cameras exhibit non-linear response at light levels below saturation. In addition to non-linearity, the response of electrostatically focused SIT cameras is greater in the center of the recorded field. This defect, known as "shading", can vary in magnitude with average illumination in some cameras. The microscope light collection and illumination paths can also contribute to shading in the image. These effects complicate the task of insuring the photometric accuracy of images obtained under different recording conditions. Newer solid-state microchannel plate intensifiers used with CCD cameras, which are free from shading effects, still are non-linear and can impose onto the low light image a repeating pattern of varying intensity (chicken wire pattern) caused by the array of microchannels. This problem has been largely overcome in the most recent intensifiers. The newest of methods employing light integration with CCD cameras are by far the most linear and free from spatial distortion than prior art designs. Integration provides the ability to image well in low light, however, the temporal resolution is compromised. Very high speed imaging systems employing two-dimensional photodiode arrays without CCD architecture, such as Neuroplex™ (Red Shirt Imaging LLC, Fairchild, Conn.), have been successfully used to monitor fast dynamics. These imagers represent a compromise between high spatial resolution and speed while providing good linearity and sensitivity. The several forms of image distortion associated with the microscope and the light detection systems must be identified and corrected, or at least shown to be insignificant, before quantitative information can be obtained using photomicroscopy.

Applications for Light Standards in Quantitative Microscopy

Aside from assessments of the performance of microscope apparatus, the main applications for a light standard in microscopy are in facilitating interpretation of quantitative data. In the life sciences, fluorescent probes of cell function produce light signals that are linked directly with ion concentrations and other cellular activity. Examples of additional areas of use are:

Cell calcium recordings—Fluorescent calcium indicators are used for quantitation of intracellular calcium concentration and time dependent changes in concentration. Fluo-3, Calcium Green, Fura Red etc. respond to calcium by changing the fluorescent yield within a single emission band without significant wavelength shifts.

Concentration must be determined by careful comparison of indicator responses under conditions of zero and high intracellular calcium, usually obtained after experimental maneuvers, or by comparison of cell readings with fluorescence from known calcium references. These calibrations do not in themselves require a standard light reference. The light standard aids this measurement by checking excitation levels to insure illumination level is safe, i.e. below a level known to give phototoxic effects, and to form a base standard that ensures repeatable experiments using the same standard. Once reproducibility is obtained, it becomes possible, under conditions where dye entering the cell attains its fluorescent property, to monitor the degree of dye loading.

Thus, the light standard facilitates reproducible experimental conditions. Calcium responses can also be compared with the light standard output, and in turn, with each other. In addition to single wavelength indicators, the calcium dye Fura-2 responds by alternating between two UV excitation bands as calcium is bound and released from the indicator. Indo-1 responds by shifting its peak fluorescence emission from 495 nm to 405 nm upon binding calcium. The calcium response is determined by the ratio of fluorescence intensities at these wavelengths. Although the signals from Fura-2 would be assessed similarly to those of the single wavelength dyes, signals from Indo-1 and Calcium Green/Fura Red dye combinations used for ratiometric recording would be assessed using light standards at two different wavelengths. For a standard based on light emitting diode (LED) sources, the calcium response indicated by the fluorescence ratio would be compared to ratios generated from the light output of blue and green LEDs (Indo-1) or green and red LEDs (Calcium Green/Fura Red). Dye fluorescence signals can be simulated if both wavelengths are combined and emitted simultaneously.

Potentiometric recordings—Voltage-sensitive dyes are also available with single wavelength and dual-wavelength responses. The most used dual-wavelength voltage dye, di-8-ANEPPS, responds with graded shifts in both excitation and emission spectra which are proportional to change in the transmembrane and membrane dipole potentials. Spectral shifts represent a departure from pure intensity changes because the fluorescence ratio is independent of the absolute fluorescence from the cell (assuming that all the dye is in the membrane being evaluated). Therefore reference light ratios from a standard can be used to compare voltage responses between different experiments and apparatus.

Prior Art of Standard Light Sources

To aid in assessing the optical performance of photo- and video-microscopes as well as the reproducibility of recordings, chemical standard light sources have been developed which are based on fluorescent microbeads, solid blocks and fluorescence filled glass capillary tubes. Beads permit the user to determine the degree to which the optical system faithfully images small three dimensional objects. Solid standards, such as uranyl glass and polymethacrylate blocks containing anthracene or rhodamine B (Starma Cells Inc.), undergo almost no photobleaching and are thus excellent tools to monitor fluctuations in excitation light levels. Solid standards have also been used to generate uniformly fluorescent fields from which to correct camera shading functions. Capillary tubes or cuvettes filled with known concentrations of fluorophores are used to characterize camera linearity, and can provide light intensities in absolute units with known excitation power, although in some cases the emission must be corrected for anisotropy. Thus, primary uses for light standards have traditionally been 1) provision of a light intensity "benchmark" for comparison between different setups, 2) assessment of the point spread or modulation transfer function, 3) assessment of detector linearity and sensitivity to a known intensity, 4) monitoring of the microscope's own illumination.

As useful as they are for quantitative work, chemical standards present some practical difficulties. Solutions must be duplicated exactly to serve as calibration light sources; thus their preparation is both time consuming and difficult and most solution standards show moderate photobleaching with use. Furthermore, in all of these standards light output is subject to change as the excitation source power changes. Thus, lamp noise from power fluctuations and aging of the burner introduce errors. Lastly, chemical standards cannot be implemented with features that allow a programmed presentation of light intensities for specific modes of operation that are useful for instrument setup, calibration, and simulation of actual measurements.

Prior Art in the Electronic Light Standard

In order to circumvent some of the problems of chemical light standards, a device employing light bars and optical feedback control of light output was designed and is disclosed in U.S. Pat. No. 5,489,771. The light bar is a style of light emitting diode (LED) that emits through a plastic diffuser, producing a relatively uniform light output. Radiance from a 1 mm circular output aperture on the diffuser surface directly in line with the internal LED chip was constant to within 2.5%. The light bar produced 6–18 mcd maximum optical power at 20 mA forward current. To avoid temperature dependant changes in emission spectra, the earlier electronics did not drive the light bar above 50% of maximum rated power dissipation. The diffuser caused over 90% of the light produced from the internal LED chip to be scattered outside the central region of uniform radiance. Some of this light was intercepted by a photodiode that provided the signal for feedback control of the light intensity. Less than 10% of the optical power passed through the output aperture, resulting in less than 2 mcd maximum output from the light standard.

The early system combined red, yellow and green light bars, each with their own output aperture, onto a holder that could be placed on the microscope stage. Output of each light bar could be set independently from a controller to produce five equally spaced intensities. Although the original device provided good performance in terms of intensity, wavelength coverage and light output uniformity, it still had several drawbacks. Light power output was insufficient for comparison with intensities produced in bright-field images and in fluorescence from many brighter dye probes such as di-8-ANEPPS and GFP. Additionally, spatial uniformity suffered from the fact that the light bar directly illuminated the aperture through a diffuser, producing a symmetric non-uniformity around the center. Therefore, not only were light bars of relatively low light conversion efficiency and power output, the light of different wavelengths could not be combined into a common output aperture. There was no provision for assessing the output of the microscope illuminator. Lastly, manual rather than programmable output settings limited the versatility of the prior art light standards.

Camera test light sources are commercially available from Advanced Illumination Inc. and can be purchased with mutli-color output capability. One light source provides a backlit field of illumination from an array of LEDs over areas of several square inches. Unevenness of the light is specified at approximately 8% over the full field. A second light source by the same company employs a hemispherical reflecting surface to produce an illuminated field with approximately the same degree of evenness and field coverage as that of the LED array illuminator. Neither system employs optical feedback control of light intensity; instead using a precision regulated current supply. Since the systems are not intended as light standards for microscopy, they are not physically adapted to mount on a microscope. Although the second system of Advanced Illumination employs a reflecting surface in the shape of a hemisphere, this design does not comprise an integrating chamber that is capable of high spatial output uniformity. Finally, neither system provides programmable test features.

BRIEF DESCRIPTION OF THE DRAWINGS

The advantages of the instant disclosure will become more apparent when read with the specification and the drawings, wherein:

FIG. 12 is a perspective representation of the disclosed system mounted on a microscope;

FIG. 13 is a cutaway side view of a chamber having a donut shaped baffle around the exit aperture;

DETAILED DESCRIPTION OF THE INVENTION

Figure 1:
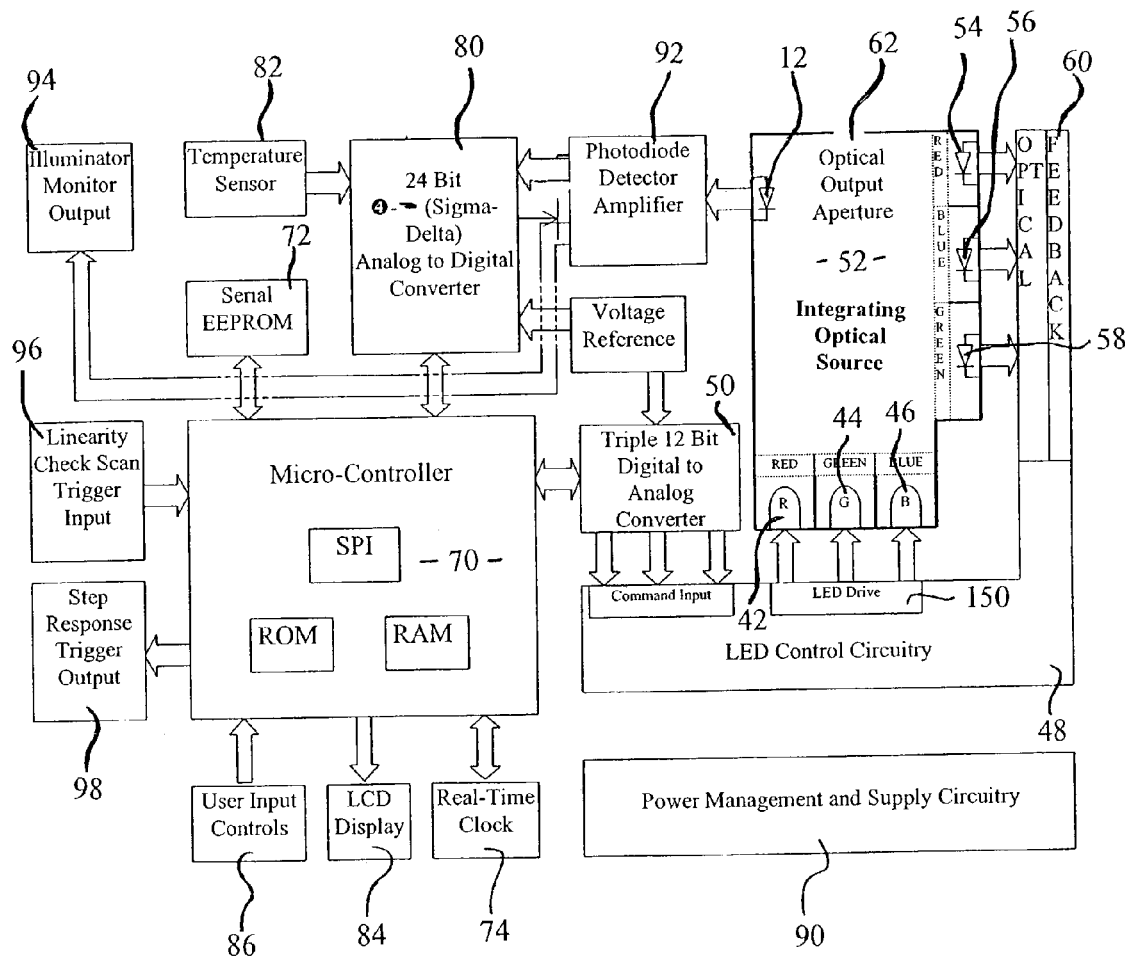
FIG. 1 is a functional block diagram of all subsystems of the light standard.

The LED based light calibration standard disclosed herein has significant technical advantages for quantitative microscopy as compared to existing chemical light standard technologies:
1. The light output is independent of the microscope's illuminator output, thereby ensuring the reliability of the base standard independent from the condition of the illuminator.
2. A defined range of calibrated light intensities is provided, ensuring easily repeatable tests.
3. Illumination is guaranteed to be even to within 2% over the microscope field of view to provide greater reading accuracy.

In addition to advances over chemical standards, the disclosed device provides greater versatility, functionality and convenience of operation over that of the previous electronic light standard art referenced above in U.S. Pat. No. 5,489,771. Improvement over this prior art include:
1. Maximum controlled light intensity is more than ten times that of the previous art, enabling calibrations for brighter light recording conditions.
2. Light of different wavelengths is provided at a common aperture that is positioned in the specimen focal plane of the microscope.
3. Wavelengths are presented independently or in combination at the aperture.
4. Specific calibration routines are incorporated to facilitate commonly used tests for characterization of microscope setups.
5. Means for monitoring and recording the intensity of a microscope's illuminator.
6. Consistency of focus in that wavelengths can be changed without the need to move the light source, thereby eliminating the need to refocus after each change.
7. Temperature stability.
8. The ability to fade from one wavelength into another.

These features, along with versatile operating modes have been heretofore unavailable in any prior art product.

Principles of Design Used to Achieve Specifications

In order to achieve higher calibrated light outputs, the disclosed design uses a high performance light source, such as "ultra-bright" LEDs, with low-angle output beams. It should be noted that although for simplicity reference hereinafter is being made to LED's, any light source having sufficient intensity, controlled light angles and spectral stability can be used. The criteria are set forth herein and any light source, such as optic fibers, that meets these criteria can be used. It is especially important that angle of the beam be sufficiently small that no rays directly exit the aperture of the integrating chamber. Methods to prevent the light beams from directly exiting the aperture are disclosed hereinafter. The light from the LEDs is then coupled to the common output aperture by an integrating chamber. This design enables multiple LEDs of different colors to simultaneously use a common aperture as opposed to the separate apertures required in the prior art. The light exiting the aperture spans the visible spectrum, including but not limited to blue, green and red wavelengths. The wavelengths of the light exiting the chamber are determined by the wavelengths of light entering the chamber, thereby enabling the disclosed optical source to work equally as well with non-visible, as well as visible, lights. In the preferred embodiment, the standard also includes a separate function for determination of the microscope's own illuminator intensity at the specimen position.

In the disclosed optical source, the direct outputs of the LEDs, which are diverging beams with gaussian intensity profiles, are converted to areas of uniform illumination through the use of an integrating chamber with an output aperture. Although an integrating sphere represents a traditional solution for producing a uniform illumination ("flat field") from sources that exhibit gaussian or otherwise non-uniform output profiles, the sphere is not adaptable for use with most microscopes. The circumference of a sphere would need to be 16 mm in diameter to provide diffuse reflecting surface to achieve flat illumination and mount the unique combination of LED and photodiode components as disclosed herein. However, because the sphere has equal height and width, a light standard based on a sphere will extend too high above the microscope stage to be universally compatible. Alternatively, a spherical light source enclosure could be mounted under the stage, but this greatly complicates the use of the microscope and is not useful for monitoring trans-illumination.

To overcome the foregoing problem with the spherical design, the disclosed device uses a cylindrical design for the light integrator. The cylindrical configuration provides an integrating surface area the same as that of a sphere in a much lower profile. As an example, a 10 mm height will accommodate the 5 mm diameter of the common T1 ¾ sized LEDs that provide sufficient power for use with the disclosed device. When other light sources are used, the chamber can be reduced proportionally. This allows compatibility with microscopes of limited working distance under the lens and evaluation of long working distance objectives.

Figure 11:
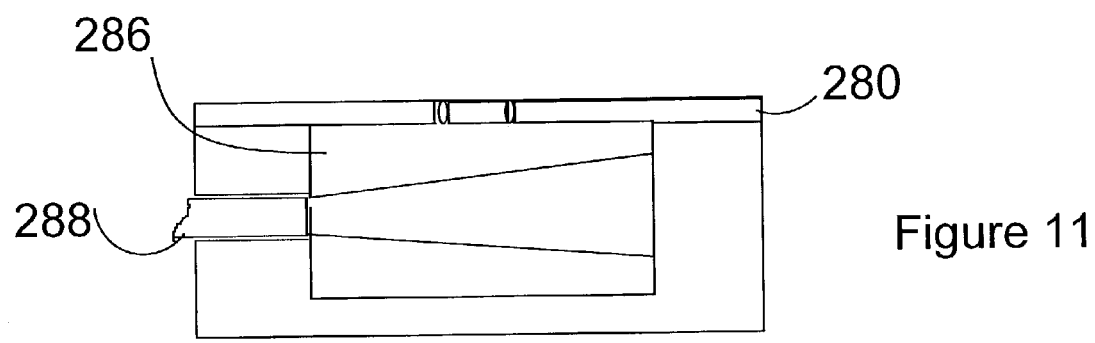
FIG. 11 is a side view of an alternate embodiment using an optic fiber as the light source.

In the disclosed device, direct radiation from the LED into the exit aperture is eliminated through the use of narrow-angle-output LEDs, or a light source of equivalent capability, placed within the wall of the light chamber. In some embodiments, a narrow hole 45, or tunnel, of about 3 mm diameter, can be used to transfer light emitted from the LED into the integrating chamber, creating a baffle to block wide angle radiation, as illustrated in FIGS. 2–4, and 10. Other methods of baffling the light source can be through any known method of controlling light ray dispersal. Whatever the light source selected, maximizing the amount of reflective, interior surface should always be a priority. The flatness of the light exiting the aperture is directly proportional to the amount of reflective inner surface. It is for this reason that the preferred embodiment for the incorporation of LED's uses the tunnel 45 to reduce the angle of the emitted beam. As an alternative to LED's, fiber can be used, as illustrated in FIG. 11 wherein the optic fiber 288 is placed almost to the interior surface of the chamber 286. If the fiber is permitted to protrude beyond the surface of the chamber, the light beams will be prevented from effectively ricocheting. Additionally, a guard ring 420, of FIG. 13, can be placed at the chamber aperture to block direct light from the LED.

The inner surface of the chamber is coated with a diffuse reflectance coating. The direction of the light emitted by each LED is randomized by repeated reflection from the coated surface, causing light at the exit aperture to be of uniform intensity across the opening. Light intensity within the chamber is monitored with an photosensor integrated circuit containing a photodiode and temperature-compensated amplifier mounted in the plane of the LEDs.

Figure 9:
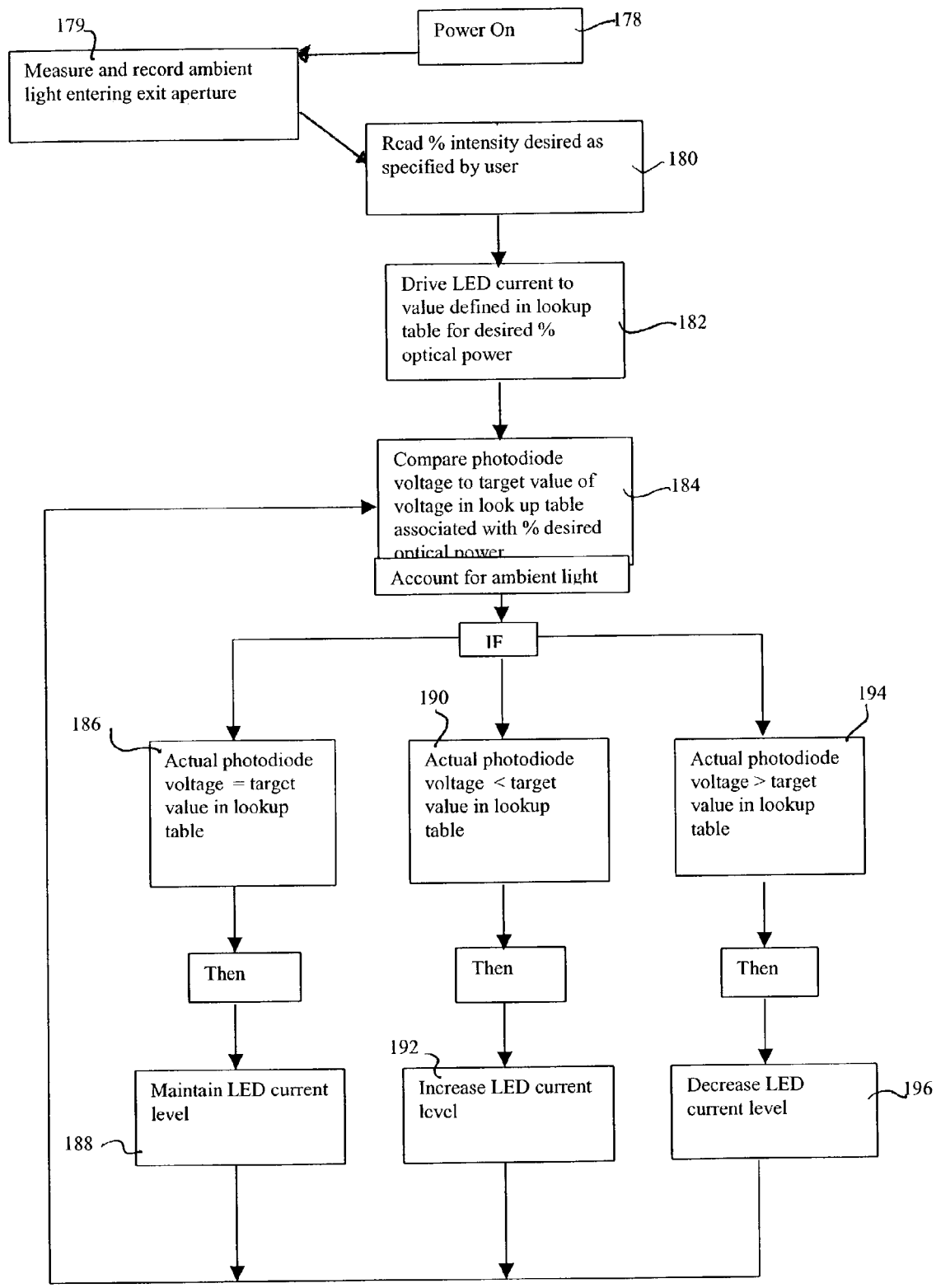
FIG. 9 is a flow chart of the light intensity control algorithm.

The light output is kept constant by a software algorithm, an example of which is illustrated in FIG. 9, executed in the microcontroller system. To begin the process of producing light of the desired wavelength and intensity, the instrument is powered on 178 and immediately checks and records the ambient light levels entering the exit aperture 179. Once the user enters operating parameters through the user interface, the instrument activates turns on the appropriate LED. The desired, or targeted, intensity is read from the user input 180 and translated to the LED drive current using a look-up table or transfer function 182. The system then "jumps" the intensity to the preprogrammed intensity that corresponds to the correlating intensity found on the look up table 182. A sample of the light that is acquired by the photosensor is compared with the photodiode voltage 184 that corresponds to the desired percentage of output intensity. Once this light sample is acquired, the system compensates, if necessary, for the ambient light readings obtained at start up 179. If the actual photosensor voltage is equal to the target value found on the look up table 186, no changes are made and the drive current remains at the same level 188. If, upon comparison, the actual photodiode voltage is less than the target value on the look up table, the drive current is increased 192 by one unit, until the photodiode voltage agrees with the table value 186. Conversely, if the photodiode voltage is greater than that found on the look up table 194, the drive current is decreased 196 decreased by one unit. To maintain the actual voltage at the target value, the system periodically checks the photosensor voltage and changes LED current to compensate for thermal drift in LEDs and ambient conditions. Therefore, once the actual voltage is equal to the targeted voltage, the system conducts this thermal compensation check by running the complete algorithm, every two seconds. The system thereby continually adjusts the LED current so that the output voltage from the photosensor corresponds to a targeted value in a lookup table, which in turn corresponds to the percentage of full light output at the aperture of the light standard that is selected by the user. It should be noted that an error window, of about ½ percent, is preferably provided to enable the target and the actual photodiode voltages to converge and prevent continual cycling of the program. Initial calibration of the light standard, which is performed at time of assembly, insures that internal lookup tables contain data that will cause the output intensity to correspond to a light level obtained from a calibrated light traceable to NIST standards.

Although there are other methods for bringing the intensity of the LED into alignment with the set value, the increase or decrease by unit is a simple, and effect, method of accomplishing the task. It should be noted that a "unit" can be defined by the manufacturer. An alternative method would be to divide the difference between the current intensity and the designed intensity by two and then subtracting or adding that amount, repeating the process until the end result, within programmed tolerances, is achieved. Other methods of alignment will be obvious to those skilled in the art.

The disclosed optical source enables enhancement of operating modes and provides a more intuitive user interface, enabling 1) the ability to select, store and recall light intensities and wavelengths (benchmark mode), 2) the generation of a sequence of increasing light intensities (linearity scan mode), 3) an intensity step output used to evaluate the transient response of detector systems (step mode), 4) the ability to have one or more wavelengths active within the chamber simultaneously (ratio light mode) and 5) ability to monitor, record and time stamp the microscope illumination at the specimen location (monitor mode). Other uses for the light chamber in conjunction with the microprocessor and graphical user interface will become apparent to those skilled in the art.

The full system is comprised of a micro-controller based electronic system 300 with a input/display module 306 having a keypad 302 and LCD display 304, and a precision optical source 308, consisting of a reflective light chamber as disclosed hereinafter, is diagramed in FIG. 12. The optical source 308 will mount on the microscope's stage 310 under the objective lens 312. The optical source 308 is connected to the main module 306 via a flexible shielded cable 314 or other hardwire or wireless method known in the art.

All data received by the micro-controller can be transferred to a PC, or equivalent, having comparison programs, graphing, etc. Alternatively, the precision optical unit can be connected directly to a PC, or equivalent, that modified with the appropriate board.

Detail of the Light Standard Subsystems

Light Source Components

In one embodiment, the user can select simultaneous output wavelengths while, in a second embodiment also disclosed, the user selects a single output wavelength.

As illustrated in FIG. 1, in the ratio light mode, the illustrated optical source consists of three ultrabright LEDs, one each of red 42, green 44 and blue 46. These LEDs are controlled by the analog drive circuitry 48 at an intensity set by the command voltages applied by the digital-to-analog converter 50. This allows for independent intensity control of each LED. The LEDs, depending upon the embodiment, radiate, either individually or together, into the integrating optical source 52 which is painted with a spectrally flat, highly reflective coating, such as Barium Sulfate (Kodak Diffuse Reflectance Coating, Kodak Co., Rochester, N.Y.; Munsell White Reflectance Coating, Edmund Industrial Optics, Barrington, N.J.).

When in the ratio light mode, each LED is monitored by a photodetector diode 54, 56, and 58, optical filters, to provide a closed feedback loop 60, an example of which is illustrated in FIG. 9, for the LED control circuit. The integrating chamber 52 homogenizes the light such that the light exiting the chamber 52 is of uniform intensity across the entire output aperture 62. The ability to independently set the wavelength and/or intensity of each LED, or change LED colors for specific applications, provides a customization that is unable to be achieved by the prior art.

A fourth multifunction photosensor 12 is also used to monitor several different conditions within the chamber. One of these functions is to evaluate changes in the microscope's built-in illuminator over time, sending the readings to the illuminator monitor output 94. The monitor photosensor 12 signal is sampled and digitized at the analog-digital converter.

It has been discovered that ambient light entering the output aperture of the light source has a significant effect on the operation of the instrument. The ambient light causes an offset in the photosensor, which produces artificially high feedback to the control loop. To overcome this problem, in the preferred embodiment the light source is enclosed within a casing to protect the electronics. Enclosure further eliminates the ability of ambient light to enter the chamber. A rugged custom molded plastic enclosure, or equivalent, is used to protect the light source electronics and shield the detectors from ambient light. In addition to the enclosure, the multi function photodetector 12 is used to sample ambient light prior to the activation of the LED's 44, 46, and 48. The amount of ambient light within the chamber 52 is sent to the microprocessor and is used as a reference that can be subtracted from the feedback signal, thereby enabling the calibration of the light source to be independent of the ambient light conditions.

Embedded Micro-Controller

One method of controlling the electronics sub-system is by a RISC (Reduced Instruction Set Computer) type independent micro-controller 70. The micro-controller 70 can be a low power complementary metal oxide semiconductor (CMOS) device with on-chip random access memory (RAM) and on-chip program store in read only memory (ROM). Other micro-controller configurations will be evident to those skilled in the art. The micro-controller 70 will communicate with peripheral components via an integrated synchronous peripheral interface (SPI). An SPI compatible EEPROM (Electrically Erasable Programmable ROM) chip 72 provides a resource for non-volatile storage of system parameters including, preset and user defined output values. A real-time clock (RTC) 74 will communicate with the micro-controller, via the SPI, to provide non-volatile time-keeping for date and time-stamping of stored data. The micro-controller will also interface with the 12-bit digital-to-analog (D/A) converters 50 that will provide discrete intensity control by changing the command voltage to each LED control circuit 48. Analog data collected from the instrument's photodiode sensor will be converted to digital information using an analog-to-digital (A/D) converter 80, having a 12-bit resolution or better. An additional input to the A/D converter can be interfaced with a semiconductor based, commercially available temperature sensor 82, which would monitor the temperature of the integrating chamber. Both the D/A and A/D converters have industry standard SPI interfaces. In order to prevent power fluctuations from reaching the micro-controller, the instrument has an on-board power management sub-system 90 to monitor and condition power supplied by an external source such as a "wall cube" type power supply.

The electronics sub-system supports a user interface consisting of a liquid crystal display (LCD) 84 and a keypad 86, or other user input controls. This will allow the user to select the instrument's mode of operation and set the intensity of the LEDs discretely between zero and full-scale power for each LED. Preset standard output values, along with other saved values, can be recalled from memory. The electronics subsystems supports TTL trigger inputs and outputs for synchronization of recording equipment with various tests. Trigger functions are enabled by the user from the user interface. The examples of trigger support illustrated in FIG. 1 include external triggering of user light detection equipment during step response tests 98 and synchronization with the user's camera during linearity scan mode 96. These capabilities provide the standard operational mode.

The optical source can be connected to a PC or equivalent, either directly or through the input/display module 306, to enable data exchange and interaction with existing stand alone and networked programs. This link is accomplished through a Graphical User Interface (GUI) to enable the setup and control of experiments from a PC where complexities of data processing and storage are more easily and powerfully managed than in the stand-alone mode. An autoranging algorithm for the feedback gain resistor is also included to improve the response of the control loop. The autoranging function improves the signal to noise ratio of the feedback signal at lower light levels and increase the stability of the control loop.

The GUI enables the user to plan an experiment and subsequently execute the experiment; save executed experiments; alter saved experiments, etc. For example, storing a sequence of light intensities used to test the microscope before a specific application where low light levels are measured; a series of dim light intensities are presented. Or a series of low, medium and high intensities are given for comparing responses on different microscopes. Another example is saving the measurements of monitor light intensity from different days.

Several applications can take advantage of simultaneous wavelength output from a light standard. One commercially important example is the synthesis of accurate color hue and saturation over a wide range of intensities. Within the scope of microscopy is ratiometric recording from fluorescent dyes. Most of the categories of physiological and cellular ion indicators include dyes for dual emission recording. Although not promoted in Molecular Probe's product literature, the voltage-sensitive dye di-8-ANEPPS has recently been employed using dual emission technique. With an optical response of ~9%/100 mV, small ratio changes on the order of 1–3% are obtained from non-excitable cells. It is challenging to do reproducible experiments with signals of this size.

The disclosed light standard provides the ability to reference each data set provided the necessary link needed for comparison of results over months of experimental recordings and changes in the apparatus. Even with larger ratio signals, as with those from cardiac action potentials, calibration is needed to provide the link of consistency between data sets from different days, where apparatus may have changed, or when comparison from different recording stations is required.

The GUI application further enables the microscopist to determine and correct for the shading function with different light collection optics by recording images of the flat-field output with a CCD camera. After correction for the light collection path, nonuniformity of illumination from the microscope light source can be determined from images of the illuminated field through the same collection optics. If the light source uses epi-illumination, a fluorescent block can be used to produce a recording. Correction for shading in illumination and in light collection paths is important for normalization of optical signals across the recorded field. The application will prompt the user to record the flat field. Using central intensity as a reference, the differential at every point is calculated and this difference image is divided by the reference value to obtain an index of nonuniformity as a function of x and y. Intensities in recorded images (either of specimen or of illumination) are corrected for shading by multiplication with the inverse of this index. To test this application, we will misalign the trans-illuminator to produce light gradients, and install a nonplanar objective. The flat-field correction for the objective will be obtained using the light standard illumination. The correction for the illuminator will then be found by recording the microscope trans-illumination, taking account of the objective correction. After this an image of a sinusoidal grating will be recorded with the microscope illumination. Uncorrected, this will exhibit nonsinusoidal variations in density. After correction for microscope optics, the corrected image of the grating will be compared with the density specification supplied by the manufacturer.

Integrating Chamber

Figure 2:
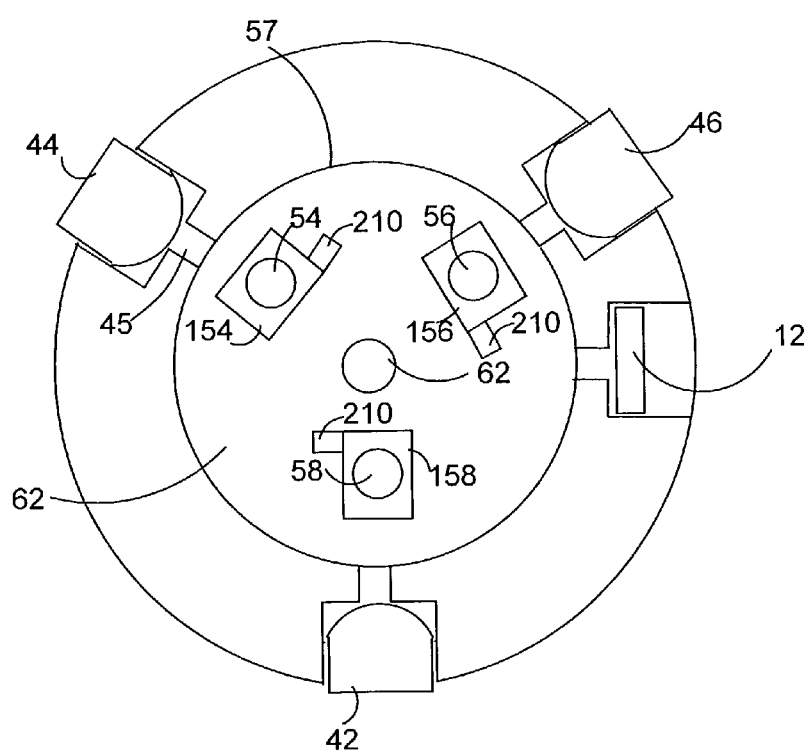
FIG. 2 is a top view of one embodiment of the remote optical source where LEDs can emit simultaneously.
Figure 3:
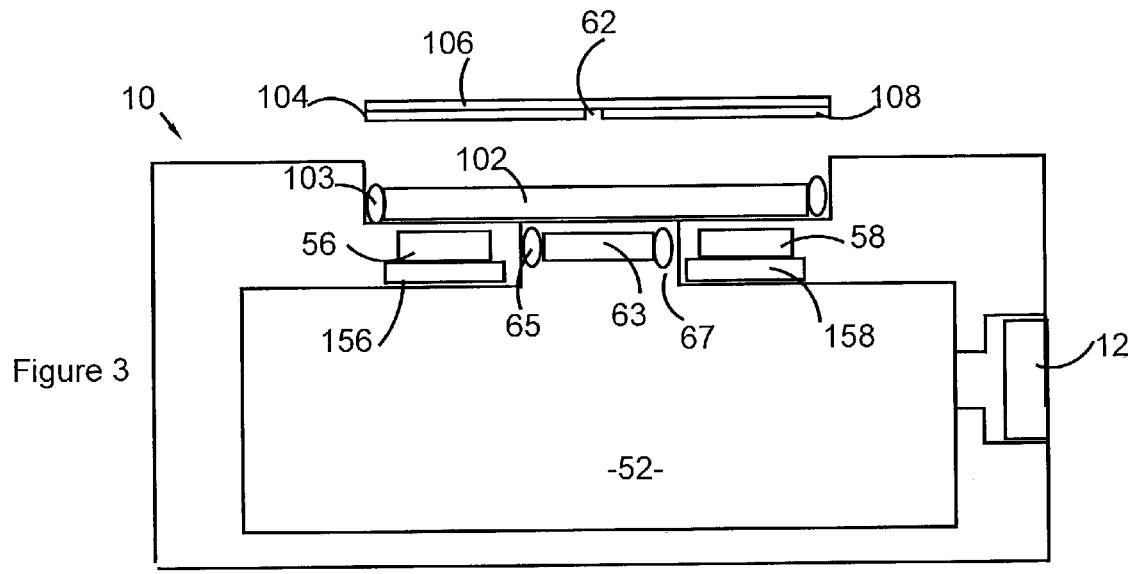
FIG. 3 is a side view of the embodiment of FIG. 2 showing the monitor photosensor and locations of filtered photodiodes.
Figure 4:
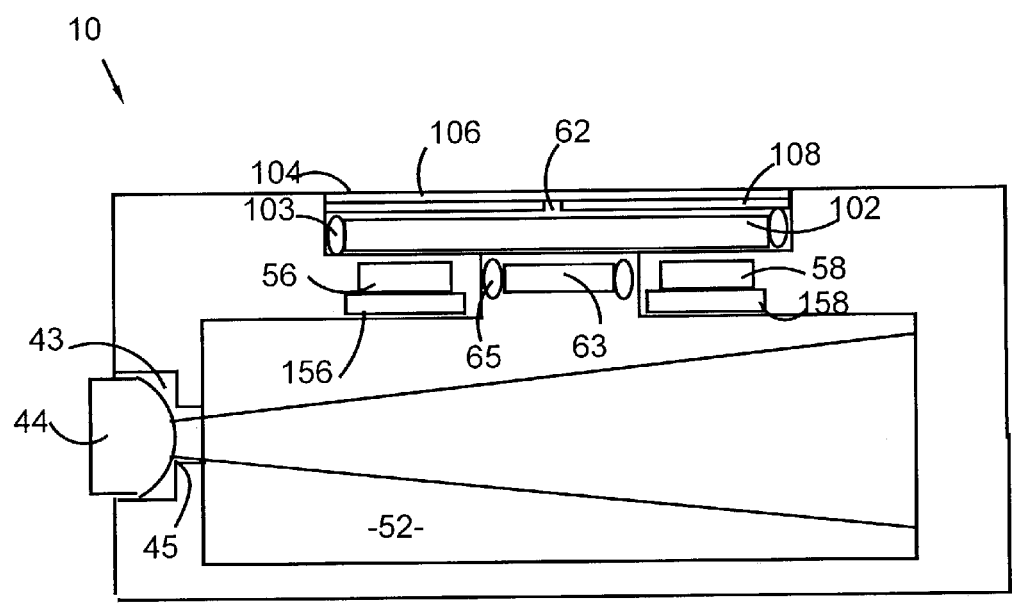
FIG. 4 is a side view of the embodiment of FIG. 2 showing an LED and locations of filtered photodiodes.

In order to improve power output and light homogeneity, flat-field illumination is implemented using a cylindrical light integrating chamber 10 shown conceptually in FIGS. 2, 3 and 4. The inner surface 57 of the integrating chamber 52 is covered with a spectrally flat coating of high reflectance paint, such as Barium Sulfate formulation from Kodak. Because of the reflective nature of the paint, emissions from an LED undergo multiple reflections in the integrating chamber 52 and uniformly distribute optical power over the inner surface with the homogenized light emitting through the circular exit aperture 62.

In these Figures, as well as in the other embodiments, the disclosed system achieves flat field illumination by precluding direct illumination of the exit aperture 62 by the LED sources. One method of accomplishing this is by allowing light to enter into the chamber 52 through a counter-bored hole 45, about 3 mm in diameter, positioned in front of the about 5 mm in diameter LED insertion hole 43. This design effectively removes the spurious light reflections from the plastic lens on the dome of the LED 42, 44 and 46, resulting in direct illumination of only a compact area of the wall opposite the LED. Other methods of dispersing light will be evident to those skilled in the art.

Tight control of the cross-sectional area of the output aperture is necessary to obtain accurate absolute calibration from the light standard. Different light flux per unit area will result if the cross section varies between devices. Since most applications will sample light from the center of the aperture (microscopy at higher magnifications), this most accurate method to insure, at time of manufacture, that the flux is the same from instrument to instrument. This requires close tolerance of the hole diameter that is machined into the optical source. One method is to use electric discharge machining, producing a well-formed 2 mm diameter hole with a ±10 $\mu$m tolerance in diameter. This deviation in the hole diameter is ~±1% of total cross-sectional area of this sized aperture, which will result in approximately the same variation in the light flux from instrument to instrument. This variation is small but still significant if instrument variability is to be controlled to less than 1%. The preferred method of manufacture is to make the exit aperture with photolithography; adding a thin optically opaque coating to glass. The clear aperture area can be made to a dimensional tolerance of ±2 $\mu$m without special techniques.

It is preferable that the aperture be covered to prevent dust and liquids etc. from entering the integrating chamber 52. In this embodiment, the top of the light source 10 is stepped in the area of the chamber exit 67 and photodiodes 54, 56 and 58 to receive the protective seal 102. Within the chamber exit 67 a clear window 63, preferably manufactured from Borafloat®, or chemically resistant equivalent, is retained through the use of lower O-ring 65. To prevent liquids and other contaminants from entering the chamber 52 around the edges of the protective seal 102, a upper O-ring 103 is used. Alternatively, the protective seal can adhered to the optical source in any manner convenient depending upon the materials of manufacture, such as screw, side clips, etc. It should be noted that although reference is made to photosensor, it should be noted that this includes photodetectors, and photodiodes, as well as any other terminology for optical sensors as known in the art.

Figure 8:
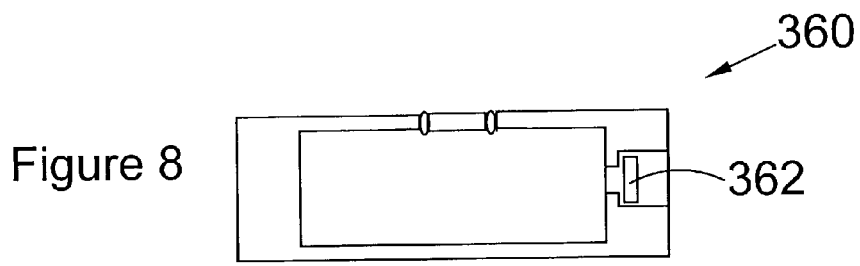
FIG. 8 is an another embodiment of the remote optical source having only the unfiltered monitoring photodiode.

Alternatively, as illustrated in FIG. 8, the entire top 280 can be removeable. This embodiment is, however, more difficult to use with the ratio light design and is preferable for the embodiments incorporating either the benchmark or the monitor, where the pass band photosensors are not required.

Depending upon the test conditions, a cover slip 104 is received on top of the protective seal 102. The cover slip 104 has an under-layer 108 of brass, or other metal, and a glass upper-layer 106. The glass upper-layer 106 is a continuous sheet of between 150 and 200 microns thickness. This layer is the same as the coverslips used by microscopists for oil and water immersion contact between the microscope objective and the specimen (in this case the specimen is the exit aperture 62). The metal under-layer 108 is no more than 20 microns thick and provides the circular opening for the exit aperture. This part can be formed by electric discharge machining or a combination of slow drill and ream of the brass shim stock sandwiched between metal pieces. The exit aperture diameter is at least 1 mm less than that of the seal 102 to prevent any reduction in light reaching the edge of the aperture. The use of an independent slip 104 provides an inexpensive replacement in the event of breakage as well as providing for easy cleaning.

Two methods are employed at the time of manufacture to check the output spatial uniformity of the integrating chamber 52. In the first method, the image of the illuminated aperture 62 is recorded on a CCD camera through a microscope using a 2.5× objective. An image of the entire aperture is obtained at the center of field where optical shading by the microscope is minimal. Values of maximum and minimum grayscales are found from the image using an image analysis program. Spatial uniformity (SU) is quantitated by the % deviation from the mean (SU= 100×(maximum I−minimum I)/mean I), where 1 signifies intensity. A second method is used to check the camera recordings. Under complete darkness, 100 ASA high resolution film is placed over the aperture and exposures made at several output settings and distances from the aperture, up to a millimeter from the surface. The film is developed and grayscale values obtained with a scanning densitometer. The value of SU is determined as above.

In cases where oil and water immersion objectives are used, cover slips must be placed between the lens and the aperture. After use, the light standard will need to be cleaned of all contact fluid. Since the cover slip sits directly over the aperture, a barrier must be used to prevent the spread of this fluid onto the aperture. A cover slip retention cap containing an o-ring seal, eliminates this concern. The cover slip will rest in a shallow detent with the cap applying slight pressure through an o-ring. Fluid will be contained by the o-ring during use. After use, contact fluid is removed by careful drying before removing the cap. A second o-ring is present in the Phase I prototype to protect the light chamber. To accommodate ronchi rulings on 1" glass slides, a 1" wide by 1 mm deep channel was added across the top of the standard. Both the top and bottom of the enclosure are then able to fit into glass slide holders, allowing the unit to be held during use on the stage of upright and inverted microscopes. The connection between the controller and source unit uses a flexible 32-guage multi-conductor cable to reduce torque on the source for added stability.

Temperature Control

The interior temperature of the chamber will affect the light conversion efficiency of the LEDs. This affect, if not compensated for, causes the light output to drift with changes in temperature. Such unwanted temperature dependency is avoided, and thus accuracy is maintained, by the use of temperature-stable and temperature-compensated detector circuits. Temperature-compensation is present in the choice of photosensors and transimpedance circuit design employed in all embodiments. The disclosed light control system thus insures that light calibration does not drift in spite of drifts in ambient temperature. In the event a non-temperature stabilized light detector is used, a thermocouple must be used to monitor the chamber temperature. In the preferred embodiment an integrated photosensor and transimpedence amplifier chip (multifunction photosensor 12), such as a Burr-Brown OPT-101, is used to maintain consistent intensity in temperature varying environments. The temperatures of the LEDs are affected by the temperatures of the chamber which is in turn affected by the ambient temperature. By using a temperature-stable photosensor, the power to the LED's can be adjusted and constant intensity can be maintained in an unstable temperature environment based upon temperature-stable photosensor voltage. In the event a non-temperature stable photodetector is used, one or more thermocouples 210 of FIG. 2, must be used to monitor the chamber temperature and would must be mounted as close to the photodiodes 54, 56 and 58 as possible.

Figure 14:
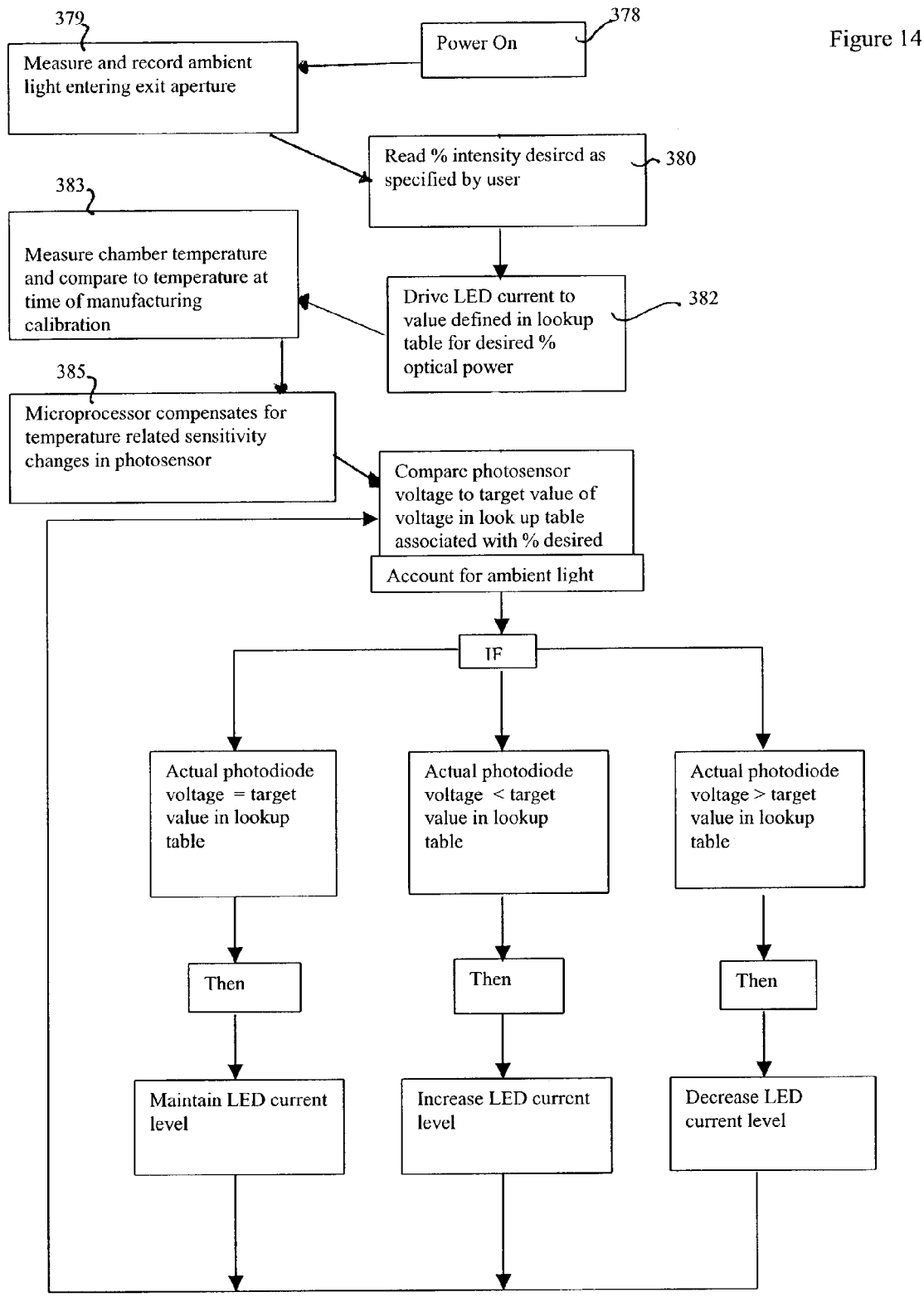
FIG. 14 is an example flow chart of a light intensity control algorithm using temperature compensation.

The temperature information is fed to the microprocessor, as illustrated in FIG. 1, and is compared with the temperature recorded when the instrument was initially calibrated by the manufacturer. The photosensor sensitivity is a function of it's current temperature, which in turn is affected by the chamber temperature. In order to maintain the calibrated intensity, the microprocessor compares the temperature related sensitivity changes in the photosensor(s), compensating the readouts accordingly. An example of an algorithm used to monitor and maintain LED intensity is illustrated in FIG. 14. As seen in this flow chart, once the unit is power on 378, the system immediately measures and records the ambient light entering the chamber 379, thereby enabling compensation when required. Once the intensity is specified 380 and the power source brought to the value programmed into the look up table 382, the system measures the chamber temperature, comparing it with the calibrated temperature at time of manufacture 383. If necessary, through the comparison, the system determines that compensation is required, the compensations will be made 385 in accordance with preprogrammed methods. The system then returns to comparing and regulating the light as described in more detail in FIG. 9.

Temperature Related Wavelength Shifts

Figure 15:
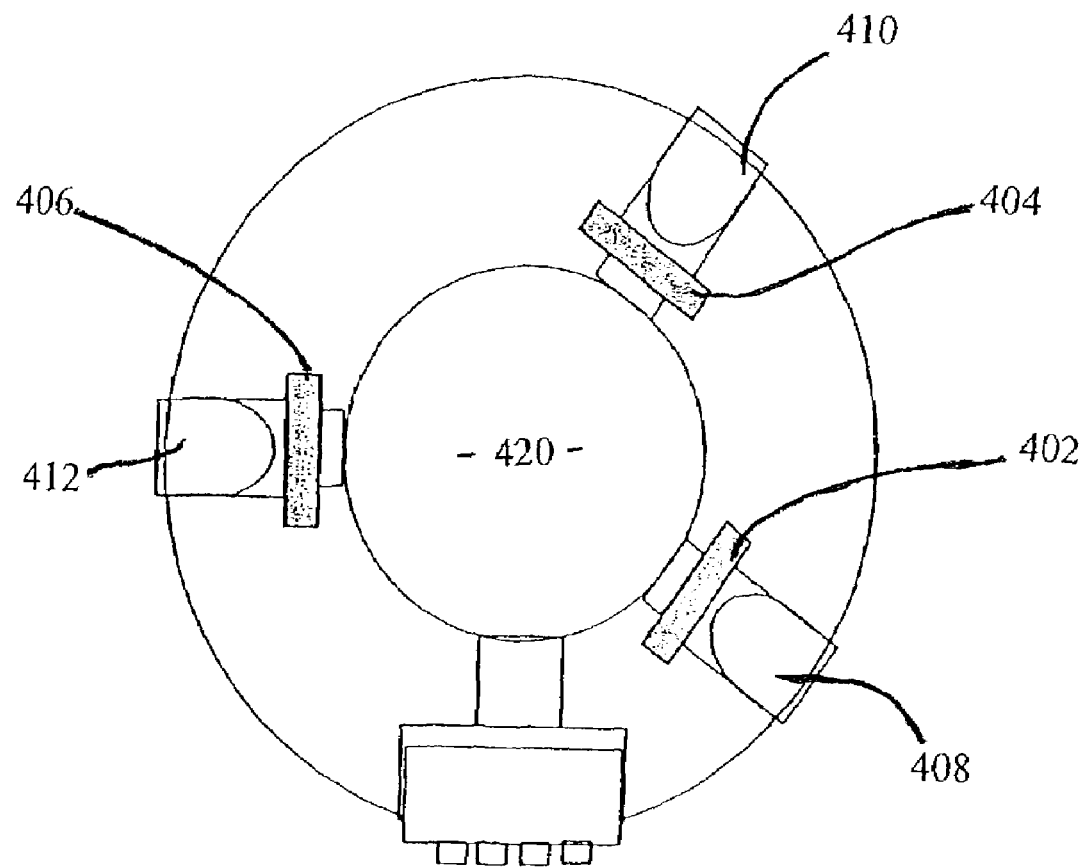
FIG. 15 is a top cutaway view of a chamber having light source filters.

As the temperature changes, the wavelengths can shift. In order to resolve this problem, one solution, illustrated in FIG. 15, is to filter the LED output before it reaches the light chamber using small (about 5×5 mm) bandpass optical filters 402, 404 and 406 between the light source 408, 410, 412 and the interior of the integrating chamber 420. The center wavelength of the filter 402, 404, 406, is placed midway into the shift interval, or 1 nm shorter than the peak output wavelength (for 2 nm shift). This allows central emission wavelengths to be transmitted, but the narrower bandwidth results in truncation of the shift. This solution will result in lower maximal output intensity, but will improve the final intensity and wavelength specifications.

Ratio Light Mode

Multiple wavelength operation of the light standard provides versatility to the instrument, increasing the number of tests that can be accurately performed. The disclosed embodiments utilize separate LEDs for each wavelength. The current technology of bi- and tri-colored LEDs are not optimal for use in the disclosed device however they can be substituted for individual LEDs appropriate applications. The power output of bi-colored and tri-colored LEDS is low, wavelength selections are limited and, most importantly, the light of each wavelength cannot be individually filtered and thus cannot be independently controlled. Until such time as these obstacles are overcome, these LED's are only usable in selected applications.

In the foregoing embodiment of the invention, illustrated in FIGS. 2–4, more than one LED is capable of being turned on at the same time due to the use of miniature photodiodes 54, 56 and 58 responsive to specific wavelength that are placed at predetermined intervals around the exit aperture 62. In most uses, the photodiodes would be placed equidistant around the aperture 62, although in some instances the spacing can be altered. The photodiodes are positioned as near as is practical to the edge of the aperture 62 in order to obtain representative readings of exiting light. Alternatively, sensors or fiber, can be place within the top facing into the exit aperture, or directly above the exit aperture, to monitor the exiting light. Precise wavelength responses are set through the use of filters 154, 156 and 158 having non-overlapping passbands being placed over each photodiode 54, 56 and 58 respectively (FIG. 2). FIG. 3 is a side view showing the photodiode/filter combinations 56/156 and 58/158 within the chamber top cover. The wavelength response so obtained for each photodiode 54, 56 and 58, and corresponding filters 154, 156, and 158, will cause only that diode to measure light from only its associated LED and remain insensitive to light from the other LEDs. This design enables control to be achieved over two or more of the LEDs as they radiate simultaneously.

The ratio light mode further permits the user to fade one wavelength into another. The user sets the wavelength decrease/increase and the lapse time and the microprocessor saves the settings for future comparison. Alternatively, the microprocessor can be programmed to calculate the increase/decrease curve with the input of the start and end intensities and the time lapse. This is advantageous as an aid for standardization of dual emission dye assays and comparison of results using ratiometric methods. A third expansion will implement new microscope illumination monitoring systems that enable the setting of illumination intensity and color balance.

Benchmark Mode

In the benchmark mode the user can set the intensity of each of the LEDs discretely between zero and full-scale power. Once a configuration is selected it can be stored in non-volatile memory and be recalled at a later time. This mode will facilitate setup of different microscope configurations with unique filter and detector parameters, by enabling comparison of recorded light readings with a known light intensity. Benchmark mode further ensures reproducible reading by allowing flat-field recordings to be performed to characterize any shading introduced by the light collecting optics or illuminator. Shading effects introduced by the microscope's light collecting optics can be evaluated from CCD recordings of the flat-field of the standard output. Once collecting optics are evaluated, non-uniformity of the illuminator is characterized by recording the trans-illumination field or epi-fluorescence from a solid block and normalizing this image by the flat-field image.

Figure 10:
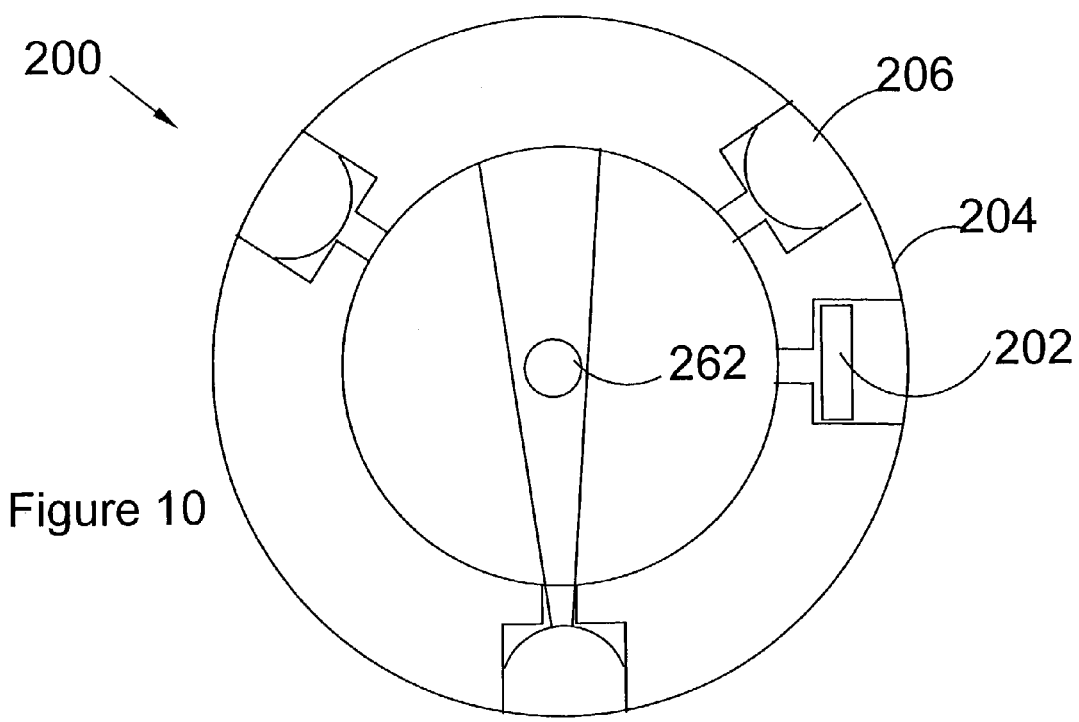
FIG. 10 is a top view of an alternate embodiment wherein one LED emits at a time within the optical chamber.

The optical source 200 for use with the benchmark mode is illustrated in FIG. 10, wherein multiple wavelengths are available, however only a single wavelength can be illuminated at a time. Since only one light source 206 can be activated at a time, the passband photodiodes can be eliminated. The light is monitored at the photosensor 202 and exits the chamber 204 through the exit aperture 262.

Monitor Mode

In the monitor mode, incident light from the microscope's illumination source is determined by measuring the light power entering the integration chamber from the objective lens. This value is stored and recalled to reproduce, and/or verify, illumination conditions used in a previous experiment. The illumination values are marked, either by reference number and/or date stamp, and stored in either the system's microprocessor or other storage device, such as an associated PC. The storage of these readings provide dual benefits. First, the prediction of illuminator failure and second, the exact reproduction of an experiment. In this mode, trans-illumination intensity is monitored by inverting the light standard to capture the focused beam from the condenser. A buffered analog output allows monitoring of fast intensity fluctuations of the microscope's illuminator on an oscilloscope. This behavior is indicative of an impending illuminator lamp failure.

In an alternate embodiment illustrated in FIG. 8, the optical source 360 is devoted strictly to the monitoring function and only contains the unfiltered photosensor 362 to read light received into the chamber through the light exit aperture. Having only the one feature in an optical source provides the advantage of reducing the expense of the multi-light sources and, for institutions, purchasing only one source containing the monitoring capabilities to share among multiple microscopes.

Figure 7:
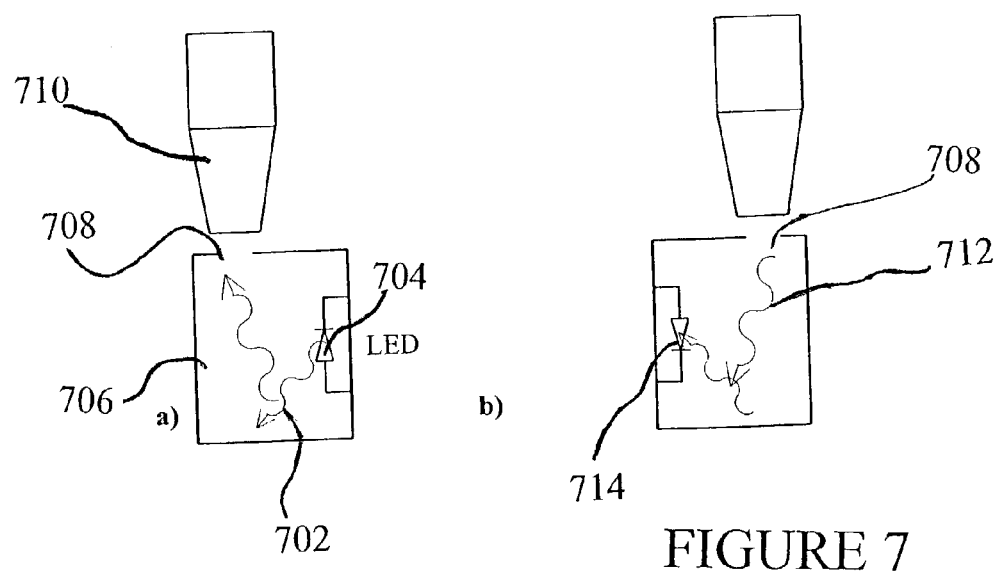
FIG. 7a operation in light emitting mode
FIG. 7b operation in illumination monitoring mode.

In FIG. 7, the difference in the travel of the light rays is illustrated. In FIG. 7a, all modes but the monitor mode, the light 702 emits from the LED 704, bounces within the chamber 706 and exits through the light exit aperture 708 and is viewed through the objective lens 710. In the monitor mode of 7b, however, the light 712 enters through the light exit aperture 708 and is read by the phodosensor 714.

Linear Scan

Figure 5:
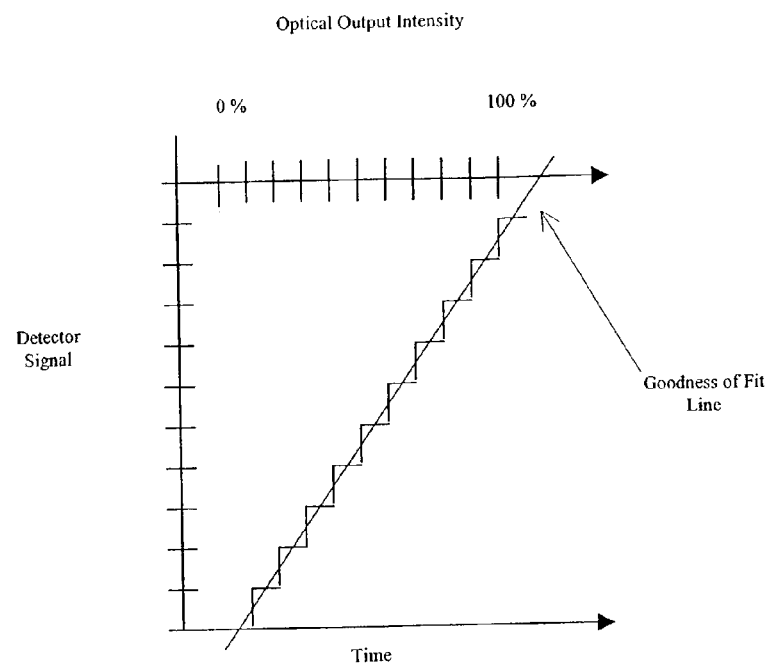
FIG. 5 is a graph illustrating a linearity scan.

In the linearity scan mode, illustrated in the graph of FIG. 5, light intensity is increased from zero in equally spaced steps while the detector or imaging system under test records light intensity. This test establishes two parameters of the light recording process: 1) linearity of response, assessed by goodness of fit with a straight line, and 2) responsivity of the detector, assessed by the slope and offset of the linear response. The stepped changes in light can be performed at equally spaced time intervals or in response to an external trigger.

Step Mode

Figure 6:
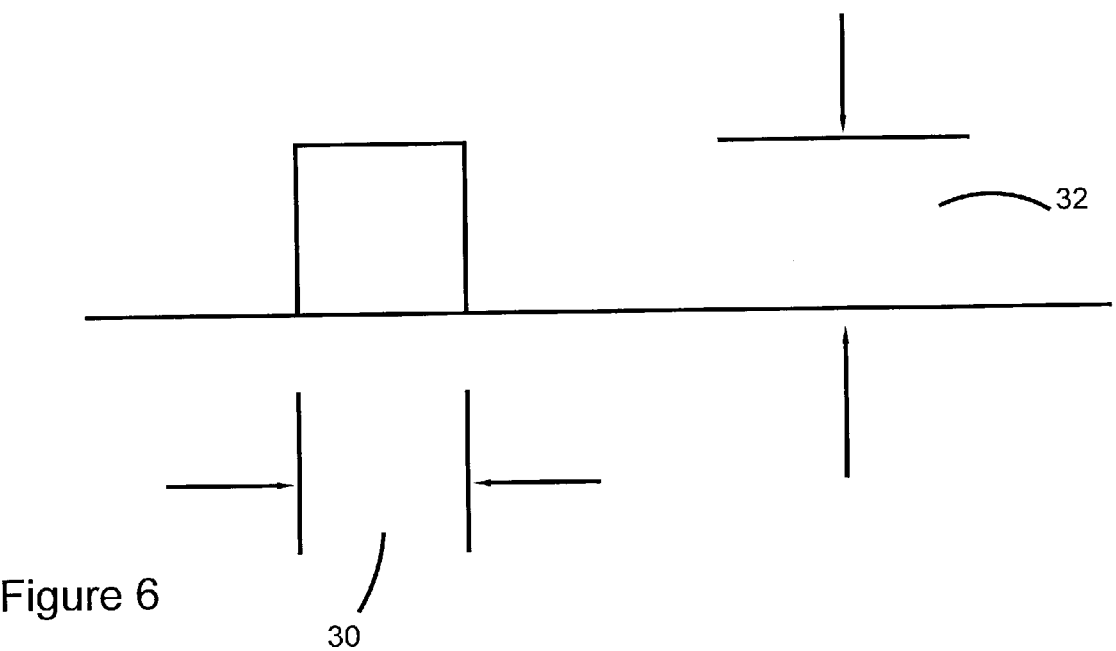
FIG. 6 is a graph illustrating a time response test signal.

In microscopy experiments, the transient response of the recording equipment is reported along with other experimental conditions. To provide for this capability, the disclosed instrument has a "step response mode" whereby pulses of light are generated at a predefined wavelength, as illustrated in FIG. 6. Pulse width 30 and amplitude 32 are entered via the user interface. This function can be used to characterize the transient response of a detector. An external trigger signal generated by the light standard triggers the detector under test simultaneously with the emitted light pulse. This external trigger can be either programmed into the software or manually activated.

Camera Gain Determination

The gain (photoelectrons/unit of digital conversion) is one of the important specifications of a digital camera for quantitative imaging since it defines the minimum change in light response that is resolved with the digitizer. Gain is usually specified for each camera by the vendor, but it can also be measured by the user. Several procedures have been developed offering either simplicity or high accuracy. The disclosed GUI application guides the user through two established procedures with his or her camera, and is intended to educate as well assist with equipment characterizations. The simplest procedure involves collection of two flat field images (FF1 and FF2) and a bias frame (zero integration time). Bias frames contain the pixel values at zero light. The gain is found from the mean value of the illumination divided by the variance of the illumination, using the expression:

$$\text{Gain} = \text{Mean}(FF1-\text{BIAS})/\text{Variance}(FF1-FF2)$$

Mortara and Fowler (1981) improved on this method by collecting flat field images at successively greater intensity, up to full scale. In a plot of the variance vs mean intensity, a line fit is made to extract both the read noise and gain from the data:

Gain=Slope

Read Noise=$(\text{y-intercept}/\text{Gain}^2)^{1/2}$

The controlled flat-field feature of the disclosed light standard works well with these techniques. Test procedures usually advise using only a small number of pixels near the center of field for flat-field data. This precaution is not necessary with the disclosed light standard; practically all the pixels receive flat illumination and thus statistical accuracy of the measurement using standard is much improved. The GUI application can also be employed by camera and sensor manufacturers for testing and quality control.

Stability and Accuracy of Reference

The accuracy and stability of the command voltage is also a key parameter in the performance of the light standard. The command voltage must be precise and accurate to insure reproducible light levels. To accomplish this the command voltage is generated by a high resolution (12-bit) DAC having an accuracy of $<\pm 0.02\%$ with a temperature coefficient of 4 ppm/° C. The DAC is referenced to a precision voltage reference with an initial voltage accuracy of $<\pm 0.05\%$ and a temperature drift of 3 ppm/° C.

To operate the LED control circuit, a percentage of full output must be specified by the user. A command voltage is sent from the micro-controller 70 to the digital to analog converter 50 and then to the LED Driver 150. From the LED Driver 150 the voltage is sent to the LED 54 (or other applicable LED) sending light into the integrating chamber 52. The photo detector 92 receives the integrated light from the LED 54 and the current converted to a voltage 156, fed back into the analog to digital converter 80 and back to the microcontroller 70, closing the control loop.

The embedded control program receives the photodiode signal and adjusts the LED current until the output of the current-to-voltage converter 156 in the feedback produces a signal voltage that is equal to the photodiode voltage given in the lookup table that is required to obtain the the requested output. At this point the embedded control program will act to stabilize and lock the intensity of the LED output in order to maintain the proper photodiode output voltage. This closed loop drive/control configuration will insure that the light intensity output of the LED will remain constant regardless of temperature drift and aging effects of the LED and integrating medium.

EXAMPLE OF SPECIFICATIONS

An example of light standard design specifications is as follows:
1. $\geq 30$ millicandelas (mcd) output minimum on all selectable wavelengths.
2. Independent control of wavelength and intensity.
3. Intensity output with a reproducibility of 0.5%.
4. Flatness of field to within 2% from center to 90% of the radius of the aperture.
5. Recallable memory of preset outputs.

6. Benchmark mode—selectable wavelengths from single aperture with discrete digital control of output intensity.
7. Linearity check mode—100 equally spaced light levels at a predefined wavelength. An external trigger input is provided.
8. Step response mode—variable output pulses having a duration of 1–1000 ms at predefined wavelength and intensity. An external trigger output is provided.
9. Microscope illumination monitor mode—monitors both direct and trans-illumination and provides a buffered analog output. This is illustrated in FIG. 7 where the difference between the light emitting mode of FIG. 7*a* and the light monitoring mode if FIG. 7*b* is illustrated.

What is claimed is:

1. A method of integrating light within a chamber, comprising the steps of:
   a. placing a first flat end of an integrating chamber on a microscope stage, said integrating chamber being a cylinder having a diffusively reflective interior,
   b. enabling light of at least one wavelength to enter said chamber through at least one light aperture from at least one light source,
   c. monitoring the intensity of said light within said chamber with a photosensor, said photosensor being recessed within the wall of said chamber and being in visual communication with said light,
   d. using a microprocessor as an input source selecting from the list of functions comprising at least one of benchmark mode, linearity scan mode, step mode, ratio light mode or monitor mode.

2. The method of claim 1 wherein one of said at least one light source is light entering through an exit aperture in a second flat end.

3. The system of claim 2 further comprising the steps of said monitor mode:
   a. measuring the light having entered said chamber through said exit aperture with said photosensor,
   b. identifying and storing the readings of said photosensor within said microprocessor input.

4. The system of claim 3 further comprising the step of recalling said readings to compare a current reading with a stored reading.

5. The system of claim 3 further comprising the step of connecting the output of said photosensor with an oscilloscope and monitoring fast intensity fluctuations of said microscope illuminator thereby predicting impending illuminator lamp failure.

6. The method of claim 1 further comprising the step of said light entering said chamber originating from a microscope illuminator.

7. The method of claim 3 further comprising the step of identifying and storing readings of said photosensor for exact reproduction of a set up of a prior experiment.

8. The method of claim 1 wherein one of said at least one light aperture is an exit aperture and another of said at least one light aperture is at least one entrance aperture recessed within the wall of, and in visual communication with, said chamber.

9. The method of claim 8 further comprising the step of said light within said chamber exiting said exit aperture as a flat field.

10. The method of claim 8 wherein said light source is at least one LED.

11. The method of claim 1 further comprising the step of processing data stored in said microprocessor to emulate fluorescence emissions.

12. The method of claim 1 further comprising the step of processing data stored in said microprocessor to emulate the ratio of fluorescence emissions of two or more wavelengths.

13. The method of claim 1 further comprising the step of processing data stored in said microprocessor to emulate at least one ratio of fluorescence emissions of a single wavelength at at least two points of time.

14. The method of claim 1 further comprising the step of characterization of a microscope light collection path and illumination path.

15. The method of claim 14 further comprising the step of said characterization being by measuring and recording optical output.

16. The method of claim 15 further comprising the step of originating said optical output from said at least one light source.

17. The method of claim 16 wherein said at least one light source is recessed within the wall of, and in visual communication with, said chamber.

18. The method of claim 16 wherein one of said at least one light source is said microscope, said microscope directing light through said light aperture to be monitored by said photosensor.

19. The method of claim 1 further comprising the step of said microprocessor monitoring gradient shifts in fluorescence intensity and ratios of intensity at one or more wavelengths.

20. The system of claim 1 further comprising the step of determining the transient response of recording equipment comprises the steps of
   a. entering width and amplitude of desired light pulses,
   b. generating said light pulses
   c. sending signals of said generated light pulses to an output device,
   thereby enabling said output device to compare the timing relationship between said generated light pulses with light pulses received by said recording device.

* * * * *